United States Patent [19]

Fischer

[11] Patent Number: 4,791,219

[45] Date of Patent: Dec. 13, 1988

[54] PREPARATION OF ETHERIFIED 3-HYDROXYVALERATES

[75] Inventor: Rolf Fischer, Heidelberg, Fed. Rep. of Germany

[73] Assignee: BASF Aktiengesellschaft, Ludwigshafen, Fed. Rep. of Germany

[21] Appl. No.: 125,567

[22] Filed: Nov. 25, 1987

[30] Foreign Application Priority Data

Nov. 27, 1986 [DE] Fed. Rep. of Germany ....... 3640595

[51] Int. Cl.$^4$ .............................................. C07C 69/66
[52] U.S. Cl. ..................... 560/187; 560/60; 560/121; 560/126
[58] Field of Search ................. 560/187, 60, 121, 126

[56] References Cited

U.S. PATENT DOCUMENTS 2,504,151  4/1950  Rehberg ............................... 560/187
2,870,195  1/1959  Heininger ............................. 560/187
4,550,195  10/1985 Platz et al. .......................... 560/206

OTHER PUBLICATIONS

ARKIV för Kemi, vol. 12, No. 25, pp. 239–246.
J. Chem. Soc. (1933), pp. 2454–2461.

Primary Examiner—Paul J. Killos
Attorney, Agent, or Firm—Keil & Weinkauf

[57] ABSTRACT

Etherified 3-hydroxyvalerates of the formula I

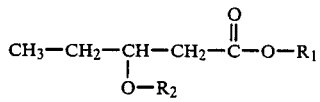

where $R_1$ and $R_2$ are identical or different and are each alkyl of 1 to 12 carbon atoms, cycloalkyl of 5 to 7 carbon atoms, aralkyl of 7 to 10 carbon atoms or aryl of 6 to 10 carbon atoms, are prepared by a process in which a 3-pentenoate of the formula II

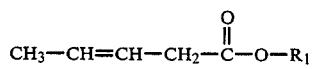

where $R_1$ has the above meanings, is reacted with a compound of the formula III

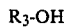

III where $R_3$ has the same meanings as $R_2$, at from 30° to 95° C. in the presence of a basic catalyst.

7 Claims, No Drawings

PREPARATION OF ETHERIFIED 3-HYDROXYVALERATES

Arkiv för Kemi, Volume 12, No. 25, pages 243 and 244 discloses that methyl 3-methoxyvalerate is obtained in a yield of 55% by reacting methyl 2-pentenoate with methanol in the presence of sodium methylate under reflux. The process has the disadvantage that the yield is unsatisfactory and furthermore starting materials which are not very cheap have to be used.

It is an object of the present invention to provide a process for the preparation of etherified 3-hydroxyvalerates in which more readily available starting materials are used and furthermore higher yields are obtained.

We have found that this object is achieved by a process for the preparation of etherified 3-hydroxyvalerates of the formula I

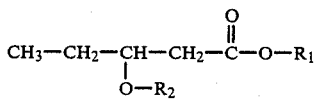     I where $R_1$ and $R_2$ may be identical or different and are each alkyl of 1 to 12 carbon atoms, cycloalkyl of 5 to 7 carbon atoms, aralkyl of 7 to 10 carbon atoms or aryl of 6 to 10 carbon atoms, wherein a 3-pentenoate of the formula II

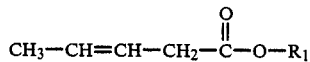     II where $R_1$ has the above meanings, is reacted with a compound of the formula III

-OH     III where $R_3$ has the same meanings as $R_2$, at from 30° to 95° C. in the presence of a basic catalyst.

The novel process has the advantages that it starts from readily available 3-pentenoates and takes place with good yields and high selectivity.

The novel process is noteworthy in that Arkiv för Kemi, Volume 12, No. 25, page 243, states that 3-pentenoic acid is not a suitable starting material since only conjugated double bonds undergo an addition reaction with an alcohol. This is confirmed in J. Chem. Soc. (1933), 2454–2461, according to which the reaction of ethyl 3-methyl-3-pentenoate with an equimolar amount of sodium ethylate in ethanol does not give the corresponding 3-ethoxyvalerate.

In the starting compounds of the formula II, $R_1$ is alkyl of 1 to 12 carbon atoms, cycloalkyl of 5 to 7 carbon atoms, aralkyl of 7 to 10 carbon atoms or aryl of 6 to 10 carbon atoms. Examples of suitable starting materials of the formula II are methyl cis- or trans-3-pentenoate, ethyl 3-pentenoate, isopropyl 3-pentenoate, cyclohexyl 3-pentenoate, benzyl 3-pentenoate, phenyl 3-pentenoate and dodecyl 3-pentenoate. In particularly preferred starting materials of the formula II, $R_1$ is alkyl of 1 to 6, in particular 1 to 4, carbon atoms, eg. methyl, ethyl, isopropyl or butyl. 3-pentenoates are obtained, for example, by the process described in U.S. Pat. No. 4,550,195. It is also possible for the resulting mixtures of isomeric pentenoates, which in addition to 3-pentenoates contain 2- and/or 4-pentenoates, to be used directly for the preparation of etherified 3-hydroxyvalerates, 2-pentenoates being converted in a similar manner while 4-pentenoates do not react and are separated off.

The reaction is carried out using compounds of the formula III in which $R_3$ is alkyl of 1 to 12 carbon atoms, cycloalkyl of 5 to 7 carbon atoms, aralkyl of 7 to 10 carbon atoms or aryl of 6 to 10 carbon atoms. Examples of suitable compounds are methanol, ethanol, n-propanol, isopropanol, n-butanol, sec-butanol, n-pentanol, decanol, cyclohexanol, cyclopentanol, cycloheptanol, phenol and phenylethanol. In preferred compounds of the formula III, $R_3$ is alkyl of 1 to 6, in particular 1 to 4, carbon atoms. Advantageously, the alcohols used correspond to those of the ester group of the starting compound II. Of course, the preferred compounds II and III give the preferred compounds of the formula I.

From 0.5 to 30, in particular from 1 to 5, moles of a compound of the formula III are advantageously used per mole of 3-pentenoate of the formula II.

The basic catalysts used are advantageously alcoholates of alkali metals or alkaline earth metals, or of aluminum or titanium.

Other suitable basic catalysts are alkali metal and alkaline earth metal amides and hydrides. Examples of suitable compounds are sodium ethylate, sodium methylate, potassium ethylate, magnesium ethylate, aluminum alcoholates and titanium alcoholates, as well as sodium amide, potassium amide, sodium hydride, potassium hydride and calcium hydride. As a rule, alcoholates derived from alcohols of 1 to 4 carbon atoms are used. Further suitable basic catalysts are strongly basic ion exchangers, for example, crosslinked polystyrene which contains quaternary ammonium groups. Alkali metal and alkaline earth metal alcoholates and strongly basic ion exchangers are particularly preferably used.

The molar ratio of 3-pentenoates of the formula II to the basic catalysts is advantageously from 1:0.01 to 1:1, in particular from 1:0.05 to 1:0.1. Reaction times of from 0.1 to 5, in particular from 1 to 2, hours are advantageously maintained.

The reaction is carried out at from 30° to 95° C., in particular from 40° to 90° C., as a rule under atmospheric pressure. However, it is also possible to employ slightly superatmospheric pressure, for example up to 10 bar. The reaction may be carried out batchwise or continuously, using a basic catalyst which is homogeneously dissolved or one which is suspended in the liquid phase.

In the batchwise procedure, the reaction is carried out, for example, as follows: A mixture of the 3-pentenoate, which may also contain 2- and/or 4-pentenoates, is heated to the stated reaction temperature with an alcohol of the formula III and the basic catalyst described above, and stirred at this temperature until the conversion is as complete as possible. The catalyst is advantageously separated off, for example by filtration or neutralization or extraction with water, and the reaction mixture is then separated by distillation.

The 3-alkoxyvalerates obtainable by the process of the invention are useful for the preparation of 3-alkoxyvaleric acids and 3-alkoxypentanols.

The Examples which follow illustrate the process according to the invention.

EXAMPLE 1

In a 500 ml three-necked flask, 228.9 g of methyl 3-pentenoate were mixed with a solution of 5.4 g of sodium methylate in 64 g of methanol (molar ratio 1:0.05:1) at room temperature, and the mixture was heated to 65°–70° C. and stirred at this temperature for 4.75 hours. After the mixture had cooled, the sodium methylate was neutralized with glacial acetic acid, and the methanol was substantially distilled off under atmospheric pressure. The residue was washed with water and then subjected to fractional distillation. This gave 185.6 g (63% of theory) of methyl 3-methoxyvalerate of boiling point 125°–126° C./304 mbar.

COMPARATIVE EXAMPLE 1

A solution of 0.4 g of sodium methylate in 4.7 g of methanol and 16.9 g of methyl 3-pentenoate (molar ratio 1:0.05:1) was heated in a glass autoclave for 4 hours at 135° C. After this time, the reaction mixture consisted of 60% of a mixture of dimethyl 2-propenylidene- and 2-(1-propenyl)3-ethylglutarate and 15% of methyl 3-methoxyvalerate.

EXAMPLE 2

A solution of 5 g of methyl 3-pentenoate and 0.12 g of sodium methylate in 50 ml of methanol (molar ratio 1:0.05:28) was refluxed for 7 hours. After this time, analysis by gas chromatography showed that the reaction mixture consisted of 55% of methyl 3-methoxyvalerate.

EXAMPLE 3

A solution of 5.4 g of sodium methylate in 64 g of methanol was added to a mixture of 192 g of methyl cis trans-3-pentenoate, 4 g of methyl 2-cis-pentenoate and 28 g of methyl 2-trans-pentenoate, and the mixture was heated to 65° C. and stirred for four hours at this temperature. After the working up procedure described in Example 1, 153.6 g (53% of theory) of methyl 3-methoxyvalerate were obtained.

EXAMPLE 4

11.4 g of methyl 3-pentenoate were added to a suspension of 20 g of a strongly basic ion exchanger in 32 g of methanol at 65° C., and the mixture was stirred for 3 hours at this temperature. Analysis by gas chromatography showed that the reaction mixture contained 60% of methyl 3-methoxyvalerate. After a reaction time of 6 hours, 65% of methyl 3-methoxyvalerate had been formed.

EXAMPLE 5

A solution of 4.8 g of sodium butylate in 74 g of n-butanol was added to 156 g of n-butyl 3-pentenoate at room temperature, and the mixture was heated to 65° C. and stirred at this temperature for 6 hours. The reaction mixture was cooled, n-butanol was distilled off, the residue was extracted by shaking with 25 ml of water, and the organic phase was dried over $Na_2SO_4$. Fractional distillation gave 95 g (41% of theory) of n-butyl 3-n-butoxyvalerate.

EXAMPLE 6

A solution of 0.3 g of 80% strength sodium hydride in 22.8 g of methyl 3-pentenoate and 6.4 g of methanol was stirred for 4 hours at 65° C. Analysis by gas chromatography showed that the reaction mixture consisted of 51% of methyl 3-methoxyvalerate.

EXAMPLE 7

When, in Example 6, the 0.3 g of sodium hydride was replaced with 0.8 g of sodium amide (50% strength in toluene), analysis by gas chromatography showed that the reaction mixture consisted of 63% of methyl 3-methoxyvalerate.

I claim:

1. A process for the preparation of an etherified 3-hydroxyvalerate of the formula I

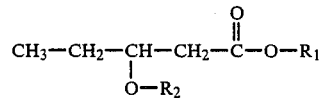

and where $R_1$ and $R_2$ are identical or different and are each alkyl of 1 to 12 carbon atoms, cycloalkyl of 5 to 7 carbon atoms, aralkyl of 7 to 10 carbon atoms or aryl of 6 to 10 carbon atoms, wherein a 3-pentenoate of the formula II

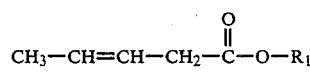

where $R_1$ has the above meanings, is reacted with a compound of the formula III $R_3$-OH     III where $R_3$ has the same meanings as $R_2$, at from 30° to 95° C. in the presence of a basic catalyst.

2. A process as claimed in claim 1, wherein the basic catalyst used is an alcoholate, amide or hydride of an alkali metal or alkaline earth metal, or a strongly basic ion exchanger.

3. A process as claimed in claim 1, wherein from 0.5 to 30 moles of the compound of the formula III are used per mole of 3-pentenoate.

4. A process as claimed in claim 1, wherein from 0.01 to 1 mole of the basic catalyst is used per mole of 3-pentenoate.

5. A process as claimed in claim 1, wherein an alkanol of 1 to 4 carbon atoms is used.

6. A process as claimed in claim 1, wherein a $C_1$–$C_4$-alkyl 3-pentenoate is used.

7. A process as claimed in claim 1, wherein a temperature of from 40° to 90° C. is maintained.

* * * * *